(12) United States Patent
Arditi

(10) Patent No.: US 6,371,914 B1
(45) Date of Patent: Apr. 16, 2002

(54) SINGLE-SHOT PHASE CANCELLATION ULTRASOUND CONTRAST IMAGING

(75) Inventor: Marcel Arditi, Geneva (CH)

(73) Assignee: Bracco Research S.A., Plan-les-Ouates (CH)

( * ) Notice: Subject to any disclaimer, the term of this patent is extended or adjusted under 35 U.S.C. 154(b) by 0 days.

(21) Appl. No.: 09/549,184

(22) Filed: Apr. 13, 2000

(51) Int. Cl.$^7$ ................................................ A61B 8/00
(52) U.S. Cl. ...................................... 600/443; 600/458
(58) Field of Search ................................ 600/443, 441, 600/442, 458, 459

(56) References Cited

U.S. PATENT DOCUMENTS

| 4,866,614 | A | * | 9/1989 | Tam | 600/437 |
| 5,526,816 | A | * | 6/1996 | Arditi | 600/458 |
| 5,961,463 | A | * | 10/1999 | Rhyne et al. | 600/458 |

* cited by examiner

*Primary Examiner*—Marvin M. Lateef
*Assistant Examiner*—Ruby Jain
(74) *Attorney, Agent, or Firm*—NIxon & Vanderhye

(57) ABSTRACT

The method of imaging the nonlinear components of ultrasound echo signals returned from scatterers comprises the steps of constructing a double-pulse excitation waveform, the two pulses composing this waveform having spectra with known relative frequency dependencies, differing in amplitude and phase so that the double-pulse waveform can be considered as a convolution of any single of said pulses with a known coding function, transmitting said double-pulse waveform within a single transmission of an ultrasound beam in the direction of said scatterers, deconvolving the received rf-waveform by a first appropriate decoding function to obtain a new rf-waveform, deconvolving said received rf-waveform by a second and different appropriate decoding function to obtain another rf-waveform, realigning in time both deconvolved rf-waveforms obtained from the same returned echo signal by a time delay as determined by the transmit-coding function, normalizing amplitudes and taking the sum of both rf-waveforms to effectively cancel all echo components caused by linear scatterers.

19 Claims, 4 Drawing Sheets

SINGLE-SHOT PHASE CANCELLATION ULTRASOUND CONTRAST IMAGING

The invention relates to a method of ultrasound imaging of organs and tissues by detection of ultrasound backscatter from a region which may contain nonlinear scatterers such as microbubbles used as a contrast agent, the method comprising projecting an ultrasound beam to a zone of tissue to be imaged, receiving the echo reflected from the tissue as a radiofrequency response signal, processing the radiofrequency response into a demodulated video output signal, storing the output in a video scan converter, and scanning the tissue to produce a video image of the region under investigation. The invention also comprises a system for ultrasonic imaging of organs or tissues which may contain nonlinear scatterers such as microbubbles used as a contrast agent, the system comprising an ultrasonic probe for transmitting and receiving ultrasonic signals, signal processing means, means for storing the processed signals and a display element. Use of the system for imaging of organs, tissues and blood vessels is also disclosed.

BACKGROUND ART

Wide acceptance of ultrasound as an inexpensive non-invasive diagnostic technique coupled with rapid development of electronics and related technology has brought about numerous improvements to ultrasound equipment and ultrasound signal processing circuitry. Ultrasound scanners designed for medical or other uses have become cheaper, easier to use, more compact, more sophisticated and more powerful instruments. However, the changes of acoustic impedance occurring within the living tissue are small and the absorption of ultrasound energy by different types of tissue (blood vessels, organs, etc.) are such that some diagnostic applications remain unmet challenges, despite these technical developments. This situation changed considerably with the development and introduction of administrable ultrasound contrast agents. Introduction of contrast agents made from stabilized suspensions of gas microbubbles or microballoons into the bloodstream and organs to be investigated have demonstrated that better and more useful ultrasound images of organs and surrounding tissue may be obtained with ultrasound equipment. Thus, pathologies in organs like the liver, spleen, kidneys, heart or other soft tissues are becoming more readily recognizable, opening up new diagnostic areas for both B-mode and Doppler ultrasound and broadening the use of ultrasound as a diagnostic tool.

Recently, ultrasound techniques, i.e. scanners, electronic circuitry, transducers and other hardware and software components are showing great progresses in their abilities to exploit, to a fuller extent, the specific properties of ultrasound contrast agents. This is made possible by the vision by ultrasound instrument manufacturers of the vast potential offered by these contrast agents towards more accurate diagnosis, thanks to enhanced imaging capabilities and quantification of blood flow and perfusion. Thus, what was almost independent developments of these related segments of the field are now providing opportunity to draw on synergies offered by studies in which the electronic/ultrasound characteristics of the apparatus and the physical properties of the contrast agent are combined. A few examples of such studies reported improvements from specific agents/equipment combinations, such as harmonic contrast imaging. These synergies are thus opening new areas of experimentation, innovation, and search of more universal methods for producing greater tissue resolution, better image and greater versatility of ultrasound as a diagnostic technique. There is no doubt that, provided their implementation is kept relatively simple, these will be widely accepted.

An attempt towards improved ultrasound imaging is described in WO-A-93/12720 (Monaghan) which discloses a method of imaging of a region of the body based on subtracting ultrasound images obtained prior to injection of a contrast agent from the images of the same region obtained following administration of the contrast agent. Based on this response subtraction principle, the method performs superposition of images obtained from the same region prior to and after administration of the contrast agent, providing an image of the region perfused by the contrast agent freed from background image, noise or parasites. In theory, the method described is capable of providing a good quality images with enhanced contrast. However, in practice, it requires maintenance of the same reference position of the region imaged for a long period of time, i.e. long enough to allow injection and perfusion of the contrast agent and maintenance of an enormous amount of data. Therefore the practical implementation of the method is very difficult if not impossible. The difficulty is partly due to inevitable internal body movements related to breathing, digestion and heart beat, and partly due to movements of the imaging probe by the ultrasound operator. Most realtime imaging probes are commonly handheld for best perception, feedback and diagnosis.

Interesting proposals for improved imaging of tissue containing microbubble suspensions as contrast agent have been made by Burns, P., Radiology 185 P (1992) 142 and Schrope, B. et al., Ultrasound in Med. & Biol. 19 (1993) 567. There, it is suggested that the second harmonic frequencies generated by non-linear oscillation of microbubbles be used as imaging parameters. The method proposed is based on the fact that normal tissue does not display nonlinear responses to the same extent as microbubbles, and therefore the second harmonics method allows for contrast enhancement between the tissues with and without contrast agent. Although attractive, the method has its shortcomings, as its application imposes several strict requirements. Firstly, excitation of the fundamental "bubble-resonance" frequency must be achieved by fairly narrow-band pulses, i.e. relatively long tone bursts of several radio-frequency cycles. While this requirement is compatible with the circuits and conditions required by Doppler processing, it becomes hardly applicable in the case of B-mode imaging, where the ultrasound pulses must be of very short duration, typically one-half or one-cycle excitation. In this case, insufficient energy is converted from the fundamental frequency to its "second-harmonic", and thus the B-mode imaging mode cannot greatly benefit from this echo-enhancing method. Secondly, the second harmonic generated is attenuated, as the ultrasound echo propagates in tissue on its way back to the transducer, at a rate as determined by its frequency, i.e. at a rate significantly higher than the attenuation rate of the fundamental frequency. This constraint is a drawback of the "harmonic-imaging" method, which is thus limited to propagation depths compatible with ultrasound attenuation at the high "second-harmonic" frequency. Furthermore, in order to generate echo-signal components at twice the fundamental frequency, "harmonic imaging" requires non-linear oscillation of the contrast agent. Such behavior imposes the ultrasound excitation level to exceed a certain acoustic threshold at the point of imaging (i.e. at a certain depth in tissue). During nonlinear oscillation, a frequency conversion takes place, causing in particular part of the acoustic energy to be converted from the fundamental excitation frequency up to its second harmonic. On the other hand, that level should not exceed the microbubble burst level at which the microbubbles are destroyed, and hence harmonic imaging will fail due to the destruction of the contrast agent in the imaging volume. The above constraints require that the imaging-instrument be set-up in such a way as to ensure the transmit-acoustic level to fall within a certain energy band: high enough to generate second harmonic components, but low enough to avoid microbubble destruction within a few cycles.

Thus, methods which treat electronic echo signals during normal realtime ("on the fly") investigations are those most desirable, allowing better imaging and wider use of ultrasound diagnostic imaging. Such methods are based on an enhancement of the echoes signals received from the regions imaged, using signal processing functions which are designed to enhance the contrast between regions containing contrast agent from those without contrast agent, on the basis of nonlinear or frequency-dependent parameters, would be simple to use and implement in new instrument designs.

U.S. Pat. Nos. 5,632,277 and 5,706,819 already disclose methods and apparatus for the detection and imaging of harmonic echo components from microbubble-based contrast agents in blood. These methods utilize first and second ultrasound pulses that are alternatively transmitted into the medium being imaged. The first and second ultrasound pulses are amplitude modulated signals in the radiofrequency range, the first ultrasound pulse differing only in sign (polarity) from the second ultrasound pulse transmitted. The echo signals generated by these successive pulses are stored in memory and combined by adding them so that the linear components cancel, leaving only the nonlinear component to be imaged. Accordingly, since tissue generally reflects less harmonic components than microbubbles, such processing enables the microbubble echoes of the contrast agent to be received with a high signal to noise ratio.

In these known approaches, for each "line-of-sight", or in other words for each ultrasound beam steering and focusing properties, a minimum of two successive pulses is required to cancel echoes from tissues while preserving significant signals of echoes from microbubbles. The radio-frequency echo signals are stored in a temporary memory following excitation of each successive pulses.

Alternative methods have been proposed in U.S. Pat. No. 5,961,463, or WO 99/30617 according to which, by alternating the polarity or otherwise coding the successive excitation conditions and taking the sum, difference or other combinations of these rf-echo signals, essentially zero signals are produced from linear reflectors other than the microbubbles, while echo signals from microbubbles produce non-linear signals that can be used to construct images with great sensitivity and enhanced contrast between microbubbles and tissues not containing a significant number of microbubbles.

There are several disadvantages common to these techniques. Firstly, because of the finite propagation velocity of sound in tissues, a time interval of several hundred microseconds must elapse between successive transmit pulses, in order for the echoes from the deepest regions of interest to return to the ultrasound probe before a following transmit pulse can be applied. This requirement limits the achievable frame rate, which is reduced in a proportion depending on the number of pulses fired in each direction, compared to similar imaging conditions without contrast-specific transmit coding. Secondly, the bubbles can move significant distances in the blood vessels in the time interval between pulses. Because of that, the resulting processing is sensitive not only to nonlinear scattering by microbubbles, but also to decorrelation due to movement between pulses. Thirdly, since the bubbles are excited successively by interrogating pulses, they can be destroyed or in other ways altered between successive pulses. As a consequence, the resulting images, Doppler or other signals are not purely dependent on the nonlinear particularities of microbubbles, but also depend on these other possible effects and artefacts.

These techniques are sometimes designated "pulse-inversion imaging", "phase-inversion imaging", "wideband harmonic imaging", "non-linear imaging using phase cancellation", etc.

SUMMARY OF THE INVENTION

The present invention pertains to a method of coding the transmitted pressure-pulse waveform in such a way as to allow decoding the resulting echo waveforms giving essentially zero contributions from linear scatterers or tissues which do not contain contrast agent microbubbles, and significant contributions for echoes originating from contrast agent microbubbles.

The present invention relates to a method of nonlinear imaging by coding the transmitted waveforms within single transmit firings of the transducer or imaging probe. It is based on the observation that in the case of reflection by linear or essentially linear scatterers such as most tissues, individual rf-echo signals can be decoded, or deconvolved, to produce essentially zero signals, while in the case of reflection by more strongly nonlinear scatterers such as contrast agent microbubbles, the same deconvolution algorithms produce significantly non-zero signals.

In this way, a sensitive method is provided to significantly enhance the contrast between tissues and microbubbles, without paying a penalty of reducing the effective pulse-repetition frequency and frame rate.

The invention also relates to a device for carrying out the above-mentioned method, comprising means for constructing a double-pulse excitation waveform, the two pulses composing this waveform having spectra with known relative frequency dependencies with respect to one another, differing in amplitude and phase in a known fashion, this waveform being intended to be applied to an ultrasound transducer to generate an ultrasonic beam, an ultrasound transducer array connected to said excitation means, comprising one or a plurality of transducer elements, a transmitter coupled to said transducer array for pulsing said transducer elements, receiving means coupled to said transducer for receiving said echo signals, means for deconvolving returned echo signal by a first appropriate decoding function to obtain an rf-waveform, means for deconvolving returned echo signal by a second and different appropriate decoding function to obtain an rf-waveform, means for realigning in time both deconvolved rf-waveforms, means for normalizing amplitudes of said deconvolved rf-waveforms, and means for summing or otherwise combining both rf-waveforms to effectively cancel all echo components caused by linear scatterers.

The invention further relates to the use of the device for detecting and imaging the nonlinear components of ultrasound echo signals returned from scatterers within the body of human patients or animals.

DETAILED DESCRIPTION OF THE INVENTION

Figure 1:
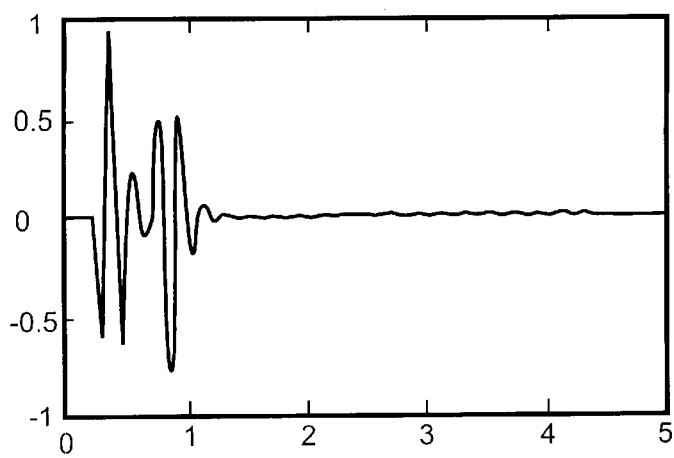
FIG. 1 is a diagram of typical single-shot phase inversion pulse.
Figure 2:
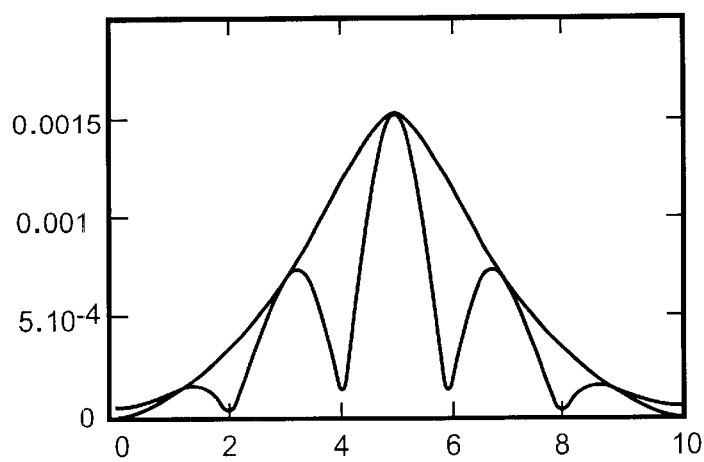
FIG. 2 is a diagram of amplitude spectra of single and double pulses.

In the disclosed implementation of this invention, a pulse waveform such as illustrated in FIG. 1 is generated by a transmit ultrasound transducer, with a center frequency at 5 MHz. The horizontal time axis is labeled in microseconds, while the vertical axis is in arbitrary pressure or voltage units. This example illustrates a double-pulse, where the second instance is inverted in polarity, delayed by 0.5 $\mu S$ and reduced by 20% in amplitude with respect to the first one. The double-pulse is constructed by summing two instances of the same model pulse, with the indicated changes in polarity, delay and amplitude; thus, the two pulses have spectra with identical relative frequency dependencies, differing only in amplitude and phase. The spectra magnitudes of the model waveform used and of the corresponding double-pulse waveform are given in FIG. 2, illustrating that the double-pulse spectrum, when normalized in amplitude to take into account its additional signal components, has as envelope the magnitude of the single-pulse spectrum, with a modulation given by the inverse of the time delay between the two pulses, i.e. $1/0.5 \mu S=2$ MHz in this example. From linear-systems theory, the double-pulse waveform of FIG. 1 can be considered as a convolution of the model single-pulse with a coding function composed of a pair of delta functions of amplitudes one and $-0.8$, separated by a time delay of 0.5 $\mu S$, as illustrated in FIG. 3.

Figure 3:
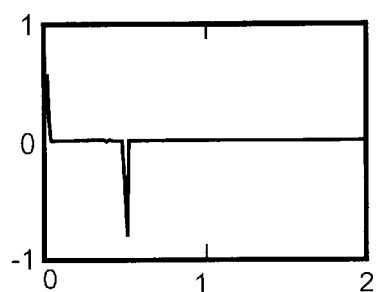
FIG. 3 is a diagram of transmit coding as delta function with respect to the first, "positive" pulse.

Deconvolution of the received echo waveforms from a collection of scatterers, such as those obtained in B-mode ultrasound imaging, can be applied in the time domain by convolution with an appropriate deconvolution kernel, or in the frequency domain by complex division by the spectrum of the coding of FIG. 3. One can thus obtain the rf-waveforms which would have been obtained from linear echoes to single-pulse excitation by the first pulse of the pulse-pair, by deconvolution of the echoes from the pulse-pair by the appropriate decoding function. Similarly, one can also obtain the rf-waveforms which would have been obtained from linear echoes to single-pulse excitation by the second pulse of the pulse-pair, by deconvolution of the same echoes from the pulse-pair by a different, appropriate, decoding function.

Figure 4:
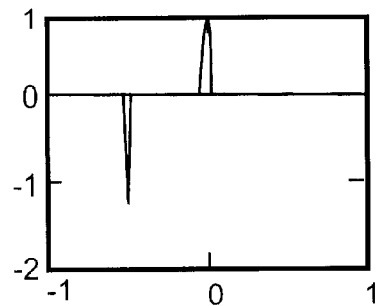
FIG. 4 is a diagram of transmit coding as delta function with respect to the second, "negative" pulse.

This different decoding function can be obtained from the observation that the pulse pair can also be considered as a convolution of the second, negative phase, pulse component by a different coding of delta function pair, as given by FIG. 4, where the first pulse is obtained by a delta function with a negative time shift and a 1/0.8, or 1.25 amplitude relative to the delta function of unity amplitude centered at the origin. In this way, and for any rf-echo signals produced by an ensemble of randomly distributed linear scatterers, it is possible, by deconvolution, to generate two rf-waveforms, equal to those that would have been obtained from the first and second pulses individually. Note that in this example, considering positive and negative pulses of different peak amplitudes allows computing the inverse of the coding spectra without any problems of discontinuities at the frequencies where zero amplitudes appear when the pulses are considered identical in amplitudes.

Figure 5:
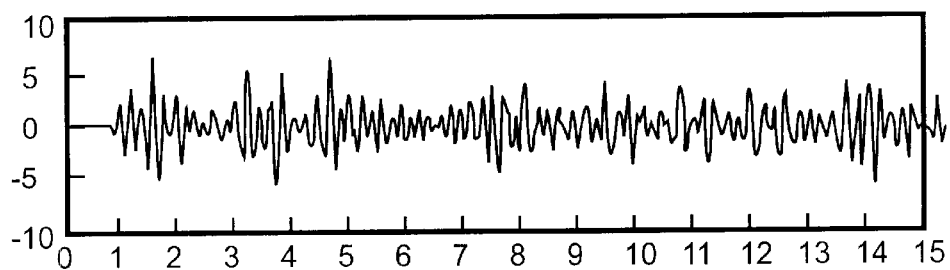
FIG. 5 is a diagram of of a typical rf-echo signal.
Figure 6:
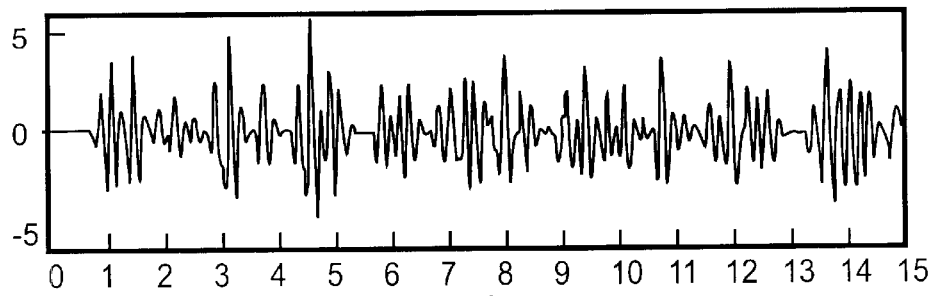
FIG. 6 is a diagram of deconvolved rf-waveform with respect to the "positive" pulse of FIG. 3.
Figure 7:
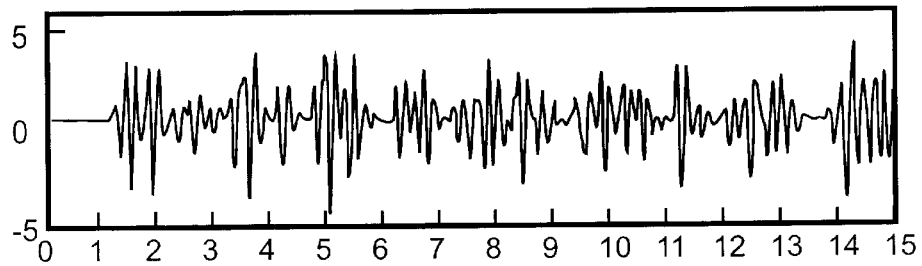
FIG. 7 is a diagram of deconvolved rf-waveform with respect to the "negative" pulse of FIG. 4.
Figure 8:
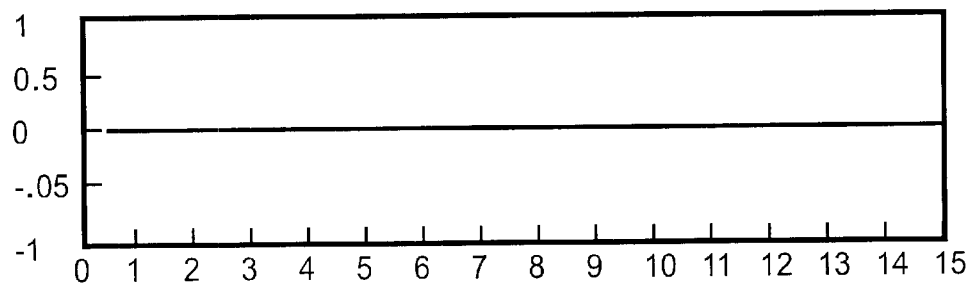
FIG. 8 is a diagram of result of single-shot phase cancellation processing for a random collection of linear scatterers.

FIG. 5 illustrates the case of a typical rf-echo signal, for linear scatterers of random amplitudes and positions along the beam propagation path, in response to the "single-shot" double-pulse coded excitation. Two different deconvolved rf-waveforms can be derived from this signal: one obtained by deconvolution with respect to a first coding sequence, as given by FIG. 3, and a second waveform obtained by deconvolution with respect to a second coding sequence, as given by FIG. 4. It is emphasized that both these resulting waveforms are derived from echoes originating from a single transmit, coded pulse waveform. The resulting rf-waveforms are illustrated in FIG. 6 and FIG. 7, respectively. The final step in the single-shot phase cancellation processing is to take the sum of both rf-waveforms, following a time shift to realign both rf-waveforms by an amount equal to the delay applied in the transmit double-pulse excitation waveform, and an amplitude normalization, again determined by that applied within the double-pulse sequence. Both these quantities can be accurately known and programmed by the control circuits and software of modern echographic instruments. The result of that sum is an essentially zero time trace signal, as illustrated in FIG. 8, indeed in agreement with what is predicted by linear systems theory for a collection of linear scatterers.

Figure 9:
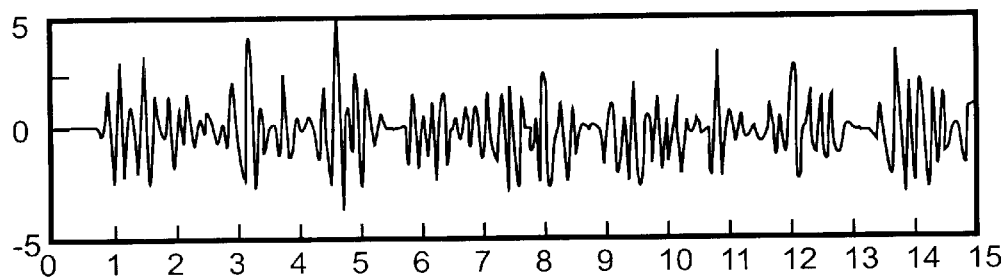
FIG. 9 is a diagram of deconvolved rf-waveform according to pulse polarity 1, with nonlinear scatterers within a limited range.
Figure 10:
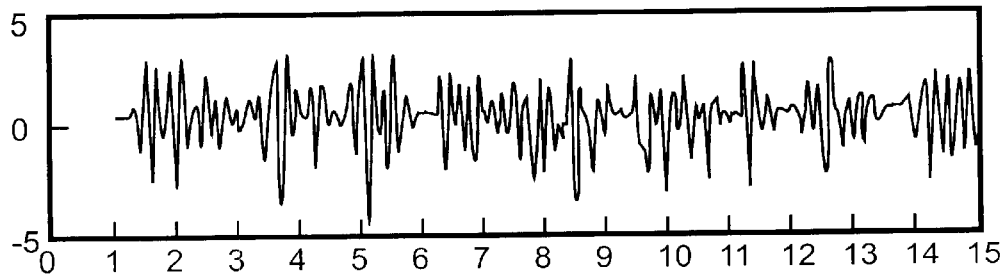
FIG. 10 is a diagram of deconvolved rf-waveform according to pulse polarity 2, with nonlinear scatterers within a limited range.

When the echo-signals are generated by non-linear scatterers as is the case in the presence of contrast agent microbubbles following intravenous injection in the organism, the deconvolutions required to obtain traces such as those in FIGS. 6 and 7 no longer produce symmetrical results, and their sums produce non-zero output signals, revealing the presence of such non-linear scatterers within the propagation path of the ultrasound excitation beam. Localization of these waveforms is found from their times of arrival, just as in the case of standard pulse-echo processing. This situation is represented in FIGS. 9 and 10, for deconvolutions according to pulse polarities 1 and 2, respectively, in the presence of nonlinear scatterers at distances corresponding to times of arrivals between approximately 5.5 and 10.5 $\mu S$.

Figure 11:
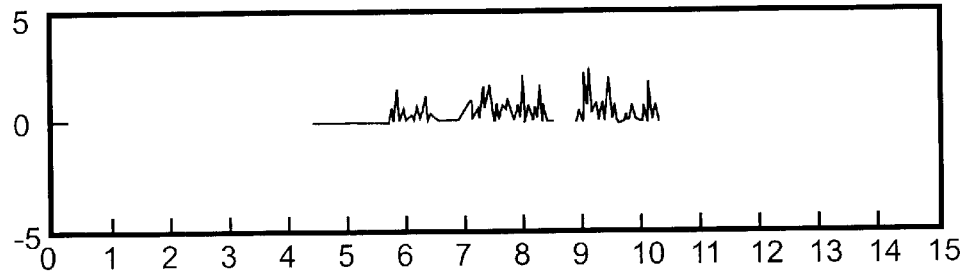
FIG. 11 is a diagram result of single-shot phase cancellation processing for a random collection of nonlinear scatterers.

FIG. 11 illustrates the type of result that can be generated from the application of single-shot phase cancellation processing along the lines described above. It can clearly be seen that the echoes arising from linear scatterers in regions outside 5.5 and 10.5 $\mu S$ are efficiently suppressed, while echoes arising from nonlinear scatterers within 5.5 and 10.5 $\mu S$ leave significant non-zero signals available for further demodulation, processing and display as a representative of the presence of contrast agent in this region.

In this way, a sensitive method is found to enhance the contrast between regions not containing in significant amounts nonlinear scatterers, and regions containing contrast agent microbubbles with significant nonlinear scattering properties, without the drawbacks of other known methods, as outlined previously. It become evident from the disclosed method of the present invention that it relates to the field of imaging processing from ultrasound echoes reflected by scatterers, so that this method is neither a method for treatment of the human or animal body, nor a diagnostic method practised on the human or animal body. Accordingly, this method is implemented by echographic imaging specialists and not by medical staff.

Figure 12:
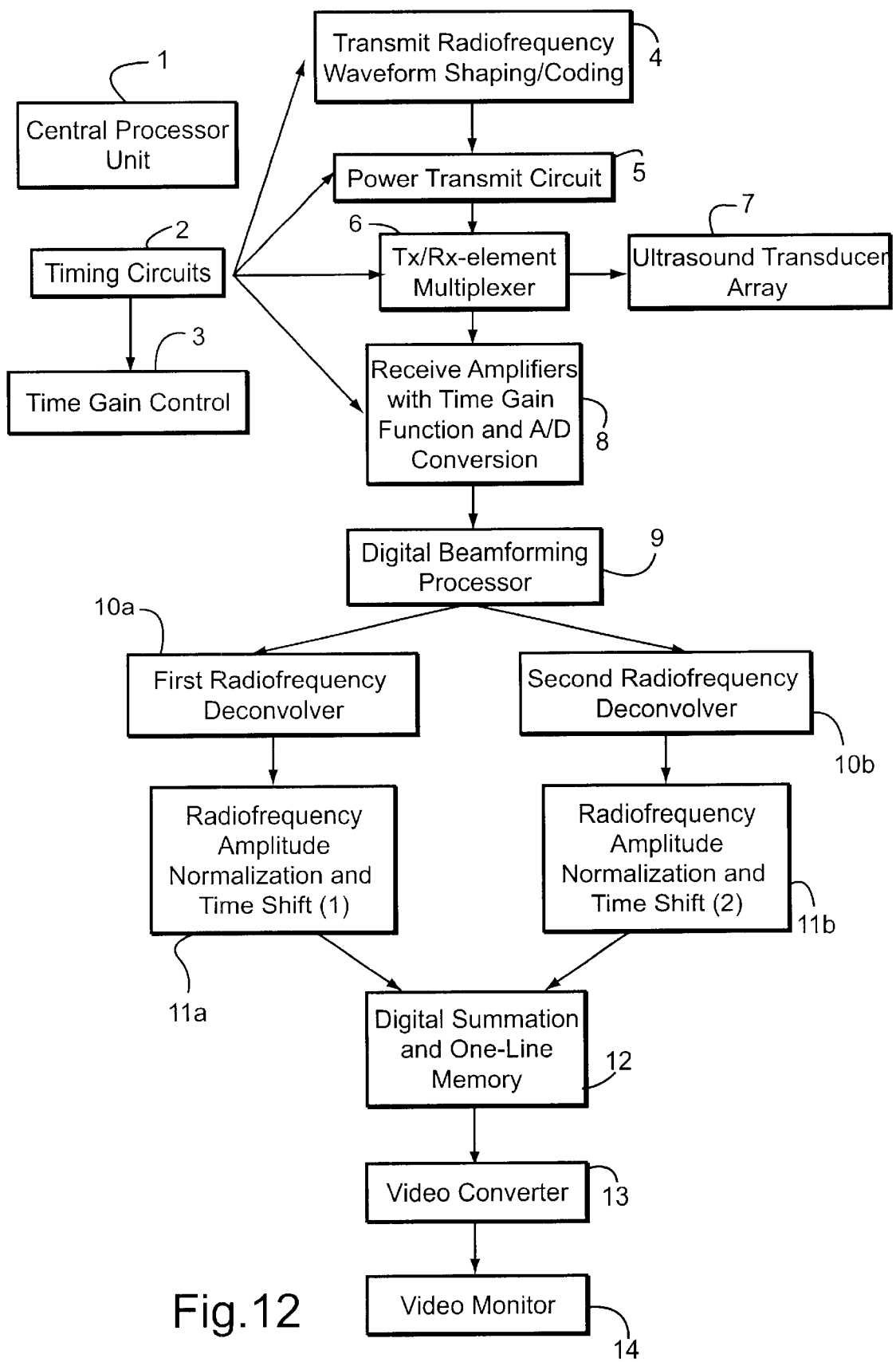
FIG. 12 is a block diagram which illustrates a contrast echography device with single-shot linear image cancellation imaging.

A typical contrast echography device of the invention, with single-shot linear image cancellation for carrying out the above disclosed method is illustrated in FIG. 12. The device includes at least the following modules: central processor unit 1, timing circuits 2, time gain control 3, transmit radiofrequency waveform shaping and coding 4, power transmit circuit 5, Tx/Rx-element multiplexer 6, ultrasound transducer array 7, receive amplifiers with time gain function and analog to digital converter 8, digital beamforming processor 9, a first radiofrequency waveform deconvolver 10a, a second radiofrequency waveform deconvolver 10b, radiofrequency amplitude normalization and time shift module 11a connected to deconvolver module 10a, radiofrequency amplitude normalization and time shift module 11b connected to deconvolver module 10b, digital summation and one-line memory 12. The output of the module 12 is connected to a video scan converter 13, connected to a video monitor 14.

In operation and under general control of a Central Processor Unit, the timing circuits 2 define a pulse repetition frequency, required for constructing echographic images (B-mode images, Doppler components in one- and two dimensions), based on sequential scanning of the region of the body to be imaged. For each successive coded-pulse excitation waveform, the timing circuits 2 also define the time-origin of a time dependent function used to provide variable amplification gain to echo signals originating from increasing imaging depths. This function is realized by the time gain control module 3, whose output can be a varying voltage, applied to gain control of the receiving amplifier with adjustable gain 8. The timing circuits 2 also allow to define transmit shaped/coded waveform, required for the adequate sequential excitation of the individual elements of the ultrasound transducer array 7 to provide beam focusing and steering to be applied to the electrical excitation power transmit circuit 5. The timing circuits also provide the signals needed to bring predefined groups of array elements into connection with the power transmit circuit 5, by ways of the connections provided by the transmit-receive element multiplexer 6. The output signals from this multiplexer are then routed to the receive amplifiers with time gain function and analog-to-digital conversion means 8, also controlled by the timing circuits 2. The digital output of these circuits 8 is fed to the digital beamforming processor 9, the output of which is fed as a common input to the processing channels for implementing waveform decoding and linear image cancellation on the returned echoes.

The example of FIG. 2 implements linear cancellation by feeding the echo signals through respectively first and second radiofrequency deconvolvers 10a, 10b, each followed by a radiofrequency amplitude normalisation and time shift 11a, 11b in order to deconvolve the echo signals from the transmit shaped/coded excitation radiofrequency waveforms. The individual outputs of the processing channels are then routed as input signals to the digital summation and one-line memory 12 for taking the sum of both rf-waveforms to effectively cancel all echo components caused by linear scatterers and produce output signals then fed to the input of the video scan converter 13, setup to write the incoming data, for each sequential pulse, in a pattern corresponding to the selected beam steering and positioning.

Thus, by repeating the above sequence at the specified rate, each time modifying the beam steering and/or focusing to obtain echoes from successive positions in the organs, tissue and blood, the scan converter output signal refreshes the image as displayed on the video monitor 14, in realtime, i.e. at a rate between a few images per second to hundreds of images per second, sufficient for reproducing perception of movement by operator of the instrument. In the process described above, the regions of the echographic images corresponding to regions containing contrast agents appear with a contrast that is vastly enhanced, because tissues reflect minimal harmonic components.

The benefits of the method and the system disclosed may equally be exploited in systems in which the processing channels are part of the receiver of a one- or two-dimensional pulsed-Doppler ultrasound system, which may further incorporate a video output representing a spectrum of velocity distribution and/or an audible signal output which is preferably a loudspeaker but it may also be any convenient sound reproducing device. Various useful options may be incorporated in the pulsed-Doppler ultrasound system such as a two-dimensional map of velocity distribution which may further be colour coded, or it may incorporate a two-dimensional map of echo amplitude or energy derived from Doppler echo components from moving targets, optionally at predetermined thresholds for velocities inferior or superior to a given value The deconvolving process may be implemented by spectral Fourier, Chirp-Z or wavelet transform analysis of returning echoes and also by applying the phase cancellation processing within a sliding time window of the returning echoes.

What is claimed is:

1. A method of detecting and imaging nonlinear components of ultrasound echo signals returned from scatterers, comprising the steps of:
   a) constructing a double-pulse excitation waveform, the two pulses composing this waveform having spectra with known relative frequency dependencies with respect to one another, differing in amplitude and phase in a predetermined manner so that the double-pulse waveform can be considered as a convolution of any single of said pulses with a known coding function, a time delay separating the two pulses being shorter than a time interval needed for ultrasound echo signals to be returned from the most distant of said scatterers to be imaged, and longer than or equal to one half period of a fundamental central frequency of any single of said pulses,
   b) transmitting said double-pulse waveform within a single transition of an ultrasound beam in a direction of said scatterers,
   c) receiving the echo signals in response to said transmitted beam returned from said scatterers to form a received rf-waveform,
   d) deconvolving said received rf-waveform by a first decoding function to obtain a new rf-waveform which would have been obtained from linear scatterers in response to single-pulse excitation by a first pulse of said double-pulse, e) deconvolving said received rf-waveform by a second and different decoding function to obtain another rf-waveform which would have been obtained from linear scatterers in response to single-pulse excitation by a second pulse of said double-pulse, f) realigning in time both deconvolved rf-waveforms obtained from the said received echo signals by a time delay as determined by said known coding function, g) normalizing amplitudes of said deconvolved rf-waveforms, h) taking the sum of both rf-waveforms to substantially cancel all echo components caused by linear scatterers and produce output signals, and i) repeating the sequence b) to h) above to project ultrasound energy in a different direction.

2. A method of detecting and imaging the nonlinear components of an ultrasound signal as described in claim 1, wherein the double-pulse excitation waveform is composed of two pulses having spectra with identical relative frequency dependencies and differing only in amplitude and phase in order to correspond to a convolution of a single of said pulses with a pair of delta functions of substantially the same amplitudes and separated by a known time delay.

3. A method according to claim 1 or 2, wherein said received echo signals are further demodulated and processed to allow their display on a video monitor as a two-dimensional map of echo-amplitudes.

4. A method according to claim 1, wherein a summation algorithm is used for processing said output signals.

5. A method according to claim 1 further comprising the step of coding said output signals by different video colors for superposition on a B-mode video display.

6. A device for detecting and imaging nonlinear components of ultrasound echo signals returned from scatterers which devices comprises:

means for constructing a double-pulse excitation waveform, the two pulses composing this waveform having spectra with known frequency dependencies with respect to one another, differing in amplitude and phase in a predetermined manner, an ultrasound transducer array connected to said excitation waveform constructing means comprising at least one transducer elements, a transmitter coupled to said transducer array for pulsing at least one transducer element to provide a transmitted beam receiving means coupled to said transducer array for receiving said echo signals, means for deconvolving returned echo signals in response to said transmitted beam by a first decoding function to obtain an rf-waveform, means for deconvolving said received echo signals by a second and different decoding function to obtain an additional waveform, means for realigning in time both deconvolved rf-waveforms, means for normalizing amplitudes of said deconvolved additional waveform, and means for summing both rf-waveforms to substantially cancel all echo components caused by linear scatterers and to produce output signals.

7. A device according to claim 6, further comprising a video scan converter coupled to said scanning means to receive said output signals.

8. A device according to claim 6, comprising analog-to-digital converter circuits connected to said at least one transducer element, whose purpose is to digitize the received echo signals to allow processing of the received echo signals by digital electronic processing circuits, and computing means.

9. A device according to claim 6, and further comprising a pulsed-Doppler ultrasound system wherein the returned echo signal processing means are adapted to be a part of said receiver of a pulsed-Doppler ultrasound system.

10. A device according to claim 9, wherein said pulsed-Doppler ultrasound system comprising a loudspeaker for outputting an audible signal.

11. A device according to claim 9, wherein said pulsed-Doppler ultrasound system comprises a spectral video output means for representing a spectrum of velocity distribution.

12. A device according to claim 11, wherein said pulsed-Doppler ultrasound system comprises a display for displaying a two-dimensional map of velocity distribution.

13. A device according to claim 9, wherein said display is adapted to provide a color coded two-dimensional map of velocity distribution.

14. A device according to claim 9, wherein said pulsed-Doppler ultrasound system display is adapted to display a two-dimensional map of echo-amplitude or energy derived from Doppler echo components from moving scatterers.

15. A device according to claim 9, wherein said pulsed-Doppler ultrasound system display is adapted to display a two-dimensional map of Doppler echo components from scatterers moving with a velocity below a predetermined threshold.

16. A device according to claim 9, wherein said pulsed-Doppler ultrasound system display adapted to display a two-dimensional map of Doppler echo components from scatterers moving with a velocity above to a predetermined threshold.

17. A device according to claim 6, wherein deconvolution means of said returned echo signals by spectral Fourier, Chirp-Z, wavelet transform analysis or direct time convolution with a deconvolution function applied within a sliding time window on the returning echoes.

18. A device according to claim 6, wherein said double-pulse waveform is constructed by a coding composed of a plurality of pulse counts higher than two, separated by known time delays and with known spectral amplitude and phase relationships between said waveforms.

19. The device according to claim 6, wherein said device is adapted for detecting and imaging the nonlinear components of ultrasound echo signals returned from scatterers within the body of human patients or animals.

* * * * *